(12) United States Patent
Horai et al.

(10) Patent No.: US 10,224,576 B2
(45) Date of Patent: Mar. 5, 2019

(54) GAS DETECTION MATERIAL, GAS DETECTION TAPE AND LITHIUM ION SECONDARY BATTERY

(71) Applicant: TDK CORPORATION, Tokyo (JP)

(72) Inventors: Takashi Horai, Tokyo (JP); Takayuki Maruyama, Tokyo (JP)

(73) Assignee: TDK CORPORATION, Tokyo (JP)

( * ) Notice: Subject to any disclaimer, the term of this patent is extended or adjusted under 35 U.S.C. 154(b) by 188 days.

(21) Appl. No.: 15/300,819

(22) PCT Filed: Jul. 2, 2015

(86) PCT No.: PCT/JP2015/069115
§ 371 (c)(1),
(2) Date: Sep. 30, 2016

(87) PCT Pub. No.: WO2016/047232
PCT Pub. Date: Mar. 31, 2016

(65) Prior Publication Data
US 2017/0025713 A1   Jan. 26, 2017

(30) Foreign Application Priority Data

Sep. 25, 2014 (JP) ................................ 2014-194791

(51) Int. Cl.
| | | |
|---|---|---|
| *H01M 10/42* | (2006.01) | |
| *G01N 31/22* | (2006.01) | |
| *B01J 20/22* | (2006.01) | |
| *B01J 20/28* | (2006.01) | |
| *H01M 2/02* | (2006.01) | |
| *H01M 2/08* | (2006.01) | |
| *H01M 10/0525* | (2010.01) | |

(52) U.S. Cl.
CPC ........ *H01M 10/4228* (2013.01); *B01J 20/226* (2013.01); *B01J 20/28009* (2013.01); *G01N 31/22* (2013.01); *G01N 31/223* (2013.01); *H01M 2/02* (2013.01); *H01M 2/08* (2013.01); *H01M 10/0525* (2013.01); *Y02T 10/7011* (2013.01)

(58) Field of Classification Search
CPC ...... H01M 2/02; H01M 2/08; H01M 10/0525; H01M 10/4228; B01J 20/226; B01J 20/28009; G01N 31/22; G01N 31/223
See application file for complete search history.

(56) References Cited

U.S. PATENT DOCUMENTS

| | | | | |
|---|---|---|---|---|
| 2009/0291328 A1* | 11/2009 | Bousseksou | ........... | B82Y 10/00 428/827 |
| 2017/0054183 A1* | 2/2017 | Kato | ................ | H01M 10/4228 |
| 2017/0276657 A1* | 9/2017 | Kato | ................ | G01N 33/0047 |
| 2017/0279168 A1* | 9/2017 | Kato | ................ | G01N 33/0047 |

FOREIGN PATENT DOCUMENTS

JP         2009-026569 A        2/2009

OTHER PUBLICATIONS

Culp, J.T., Chen, D-L, Liu, J., Chirdon, D., Kauffman, K., Goodman, A., Johnson, J.K.—Effect of Spin-Crossover-Induced Pore Contraction on CO2-Host Interactions in the Porous Coordination Polymers (Fe(pyrazine)M(CN)4)(M=Ni, Pt), Eur, J. Inorg. Chem, 2013, pp. 511-519 (Year: 2013).*
Asai, Y, Onishi, K., Miyata, S., Kim, S-J, Matsumoto, M., Shigeara, K.—Octacyanophthalocyanatoiron Polymer as Cathode Material for a Secondary Lithium Battery, Journal of the Electrochemical Society, 148(4), A305-310, 2001 (Year: 2001).*
Boldog, Ishtvan et al., "Spin-Crossover Nanocrystals with Magnetic, Optical, and Structural Bistability Near Room Temperature," Angewandte Chem. Int. Ed., (2008), vol. 47, No. 34, pp. 6433-6437.
Niel, Virginie et al., "Cooperative Spin Crossover Behavior in Cyanide-Bridged Fe(II)-M(II) Bimetallic 3D Hofmann-like networks (M=Ni, Pd, and Pt)," Inorg. Chem., (2001), vol. 40, No. 16, pp. 3838-3839.
Southon, Peter D. et al., "Dynamic Interplay between Spin-Crossover and Host-Guest Function in a Nanoporous Metal-Organic Framework Material," Journal of American Chemical Society, (2009), vol. 131, No. 31, pp. 10998-11009.
Aug. 18, 2015 Search Report issued in International Patent Application No. PCT/JP2015/069115.

* cited by examiner

*Primary Examiner* — Anca Eoff
(74) *Attorney, Agent, or Firm* — Oliff PLC

(57) ABSTRACT

A gas detection material having a Hofmann type porous coordination polymer of $\{Fe(pz)[Ni(CN)_4]\}$ (wherein, pz=pyrazine) which contains ferrous ion, tetracyanonickelate ion and pyrazine as the essential ingredients and has a pillared crystal shape. Also a lithium ion secondary battery, wherein, the outer package of the lithium ion secondary battery is covered by the gas detection material mentioned above.

9 Claims, 3 Drawing Sheets

GAS DETECTION MATERIAL, GAS DETECTION TAPE AND LITHIUM ION SECONDARY BATTERY

The present invention relates a gas detection material, a gas detection tape and a lithium ion secondary battery.

BACKGROUND

A lithium ion secondary battery is lighter in weight and has higher capacity than a nickel-cadmium battery, a nickel hydride battery, and the like. Thus, lithium ion secondary batteries are widely used as a power supply for portable electronic devices. The lithium ion secondary battery is also a strong candidate for a power supply mounted on hybrid automobiles or electric automobiles. With the decrease in size and increase in functionality of portable electronic devices in recent years, the lithium ion secondary battery used for the power supply is expected to have higher capacity.

Lithium ion secondary batteries can be made into various forms and a prismatic lithium ion secondary battery, a pillared lithium ion secondary battery and a pouch-type lithium ion secondary battery can be listed as the representative ones.

Among these batteries, the pouch-type lithium ion secondary battery uses a pouch-type case made by sheets, thus, it is light and can be manufactured into various forms of lithium ion secondary batteries. And there is also a strong point in the simple manufacturing process. On the other hand, in the pouch-type lithium ion secondary battery uses a pouch-type case, thus, there is a problem that it is weak to the swelling caused by a flaw or an increase in the inner pressure. The increase in the inner pressure of the lithium ion secondary battery is considered to be caused mainly by the evaporation of the electrolyte solution or the decomposition gas of electrolyte solution.

As the electrolyte solution of the lithium ion secondary battery, it is usually made by mixing a ring carbonate such as ethylene carbonate, a chain carbonate such as diethyl carbonate and adjusting to the desired relative permittivity or viscosity. As the chain carbonate has a lower boiling point, if there is a flaw such as a pinhole in the pouch-type case caused by any reasons in the manufacturing process of the pouch-type lithium ion secondary battery, a part of the electrolyte solution will become vapor and be evaporated and it will result in a bad smell and bad influences such as that the expected discharged capacity cannot be obtained. In addition, when the battery is over-heated or placed under a high temperature, evaporation or a decomposition reaction will happen to the electrolyte solution and the inner pressure will be raised so that swelling will be terrible. Sometimes, the vapor of the electrolyte solution or the decomposition gas of the electrolyte solution will leak from the pouch-type case and the discharged capacity will decrease similarly. Further, problems will rise not only in the safety or the property of the battery, but also may influence the cellular phone or the notebook computer or the like using the battery greatly.

Usually, when the manufactured batteries are to be sold, detection will be provided and the batteries in which leaked gas of electrolyte solution or the like is produced will be picked out. Accordingly, various detection methods for leaked gas of the battery are proposed up to the present.

For example, in Patent document 1, a detection method is proposed for detecting the leaked detection gas from the hermetic battery using a gas sensor by manufacturing a hermetic battery in a hermetically sealed container with the detected gas atmosphere such as helium or argon or the like and then removing the detected gas in the hermetically sealed container followed by decompressing.

However, in the detection method of Patent document 1, a hermetically sealed container is required in the manufacturing process, thus, not only the instrument will be in a large scale, but also a detected gas supplying, pressure reducing devices and processes such as sensing for detected gas using a sensor are required. Therefore, there is a problem that the detection cannot be carried out simply. Further, there is a problem that the gas leakage before or after the detecting process cannot be detected.

PATENT DOCUMENTS

Patent Document 1: JP2009-26569A

Non-Patent Documents

Non-Patent Document 1: Inorganic Chemistry, 2001, Vol 40, p. 3838-3839.
Non-Patent Document 2: Angewante Chemie International Edition, 2008, Vol 47, p. 6433-6437,
Non-Patent Document 3: Journal of the American Chemical Society, 2009, Vol 131, p. 10998-11009.

SUMMARY

A self-assembled regular complex with a high molecular weight from metal ions and organic ligands is called as a porous coordination polymer. A Hofmann type porous coordination polymer has a structure with a grown jungle gym type skeleton and has countless spaces in its inner part. Thus, it is well known for its adsorption for various molecules or the like. In Non-Patent Documents 1 to 3, a phenomenon called as spin crossover is described which is happened in a porous coordination polymer with specific structure, wherein the magnetic property varies between two states which are called as high-spin state and low-spin state by external factors such as heat, light, the adsorption of molecule or the like. A gas detection material can be made using this phenomenon, but no specific application examples exist until now.

The present invention is completed from the problems mentioned above and aims at providing a gas detection material, a gas detection tape which can detect the leaked gas easily without using a large-scale detection instrument, and a lithium ion secondary battery having the gas detection material.

In order to solve the problems mentioned above and reach the aim, the gas detection material of the present invention is characterized in that it contains a Hofmann type porous coordination polymer of $\{Fe(pz)[Ni(CN)_4]\}$ (wherein, pz=pyrazine) which contains ferrous ions, tetracyanonickelate ions and pyrazines as the essential ingredients and it has a pillared crystal shape.

Leaked gas can be detected easily by using the gas detection material without using a large-scale detection instrument.

Further, it is preferred that a part or all of the gas detection material of the present invention is in the low-spin state.

Furthermore, the gas detection material of the present invention is preferred to contain acetonitrile.

In addition, the gas detection tape of the present invention is a gas detection tape made by disposing a gas detection material on at least one surface of the supporter, wherein, the gas detection material is characterized in that it contains a Hofmann type porous coordination polymer of {Fe(pz)[Ni(CN)$_4$]} (wherein, pz=pyrazine) which contains ferrous ions, tetracyanonickelate ions and pyrazines as the essential ingredients and it has a pillared crystal shape.

Further, the lithium ion secondary battery of the present invention is characterized in that the gas detection material or the gas detection tape is disposed on the surface of the outer package of the lithium ion secondary battery.

According to the present invention, a gas detection material, a gas detection tape which can detect the leaked gas easily without using a large-scale detection instrument, and a lithium ion secondary battery having the gas detection material can be provided.

DETAILED DESCRIPTION OF EMBODIMENTS

Hereinafter, the embodiments of the present invention will be described in detail with reference to the drawings. However, the present invention is not restricted by the contents disclosed in the following embodiments.

The gas detection material contains a Hofmann type porous coordination polymer of {Fe(pz)[Ni(CN)$_4$]} (wherein, pz=pyrazine) which contains ferrous ions, tetracyanonickelate ions and pyrazines as the essential ingredients and it has a pillared crystal shape.

Figure 1:
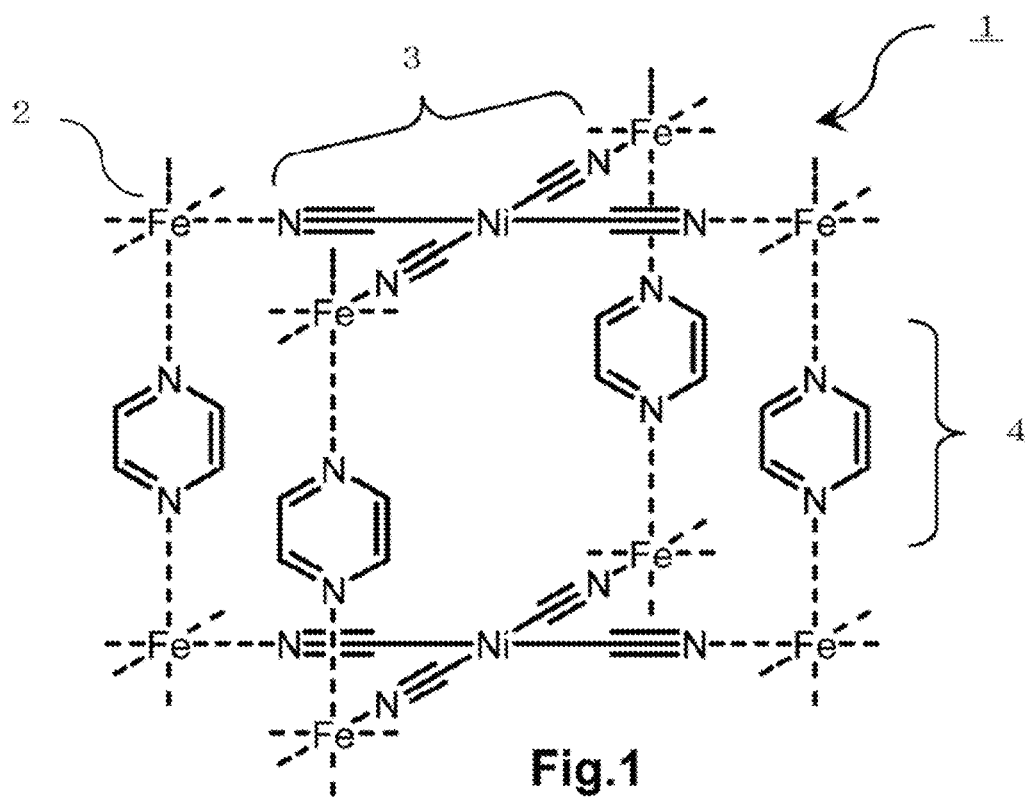
FIG. 1 is a schematic view showing the primary chemical structure of the Hofmann type porous coordination polymer of the present invention.

As shown in FIG. 1, {Fe(pz)[Ni(CN)$_4$]} 1 (wherein, pz=pyrazine) has a structure in which tetracyanonickelate ion 3 and pyrazine 4 are self-assembly regularly coordinated onto ferrous ion 2 and the jungle gym type skeleton grown, wherein the inner space can absorb varies of molecules or the like. In addition, in {Fe(pz)[Ni(CN)$_4$]} (wherein, pz=pyrazine), a phenomenon called as spin crossover is noticed, wherein the electron configuration of ferrous ions varies between two states which are called as high-spin state and low-spin state by external stimulations such as heat, pressure, or the adsorption of molecule. The spin variation can be considered to be in several tens of nano-seconds and has a character of a very high response speed.

The high-spin state refers to the state where the electrons are configured in a way that the spin angular momentum becomes the biggest according to the Hund's rule in the 5 orbits of the d electron of the ferrous ions in the complex. The low-spin state refers to the state where the electrons are configured in a way that the spin angular momentum becomes the smallest. The two states are different in the states of the electron and the crystal lattices, thus, the colors and the magnetisms of the complexes in the two states are different. That is, if the spin crossover phenomenon caused by the adsorption of the molecule of {Fe(pz)[Ni(CN)$_4$]} (wherein, pz=pyrazine) is used, the molecule can be used as the detecting material which can detect specific molecules expeditiously.

The {Fe(pz)[Ni(CN)$_4$]} (wherein, pz=pyrazine) in the high-spin state is an orange crystal and it will turn to reddish purple of the low-spin state if it is cooled sufficiently by liquid nitrogen or the like. In addition, if it is exposed in the gas of specific organic compounds such as acetonitrile or acrylonitrile or the like, the gas will be adsorbed into the inner of the crystal and the {Fe(pz)[Ni(CN)$_4$]} (wherein, pz=pyrazine) will turn to be the low-spin state. If the reddish purple crystal of the {Fe(pz)[Ni(CN)$_4$]} (wherein, pz=pyrazine) in the low-spin state is exposed in the organic compound gas other than the specific organic compound which induces the low-spin state, it will take gas into the inner of the crystal and turn to be an orange crystal of the high-spin state by the spin crossover phenomenon. As the gases of the organic compounds, vapors such as organic combustible gas or volatile organic solvent or the like can be listed as examples. That is, when the {Fe(pz)[Ni(CN)$_4$]} (wherein, pz=pyrazine) in the low-spin state is in an atmosphere with gas of an electrolyte solution for lithium ion secondary battery such as dimethyl carbonate (hereinafter, referred as DMC), diethyl carbonate (hereinafter, referred as DEC), and ethyl methyl carbonate (hereinafter, referred as EMC) or the like or gas(es) such as ethylene and propylene or the like which is/are produced by the decomposition of the electrolyte solution mentioned above existing, the {Fe(pz)[Ni(CN)$_4$]} (wherein, pz=pyrazine) will adsorb these gases, and change orange in the high-spin state. Thus, it can be easily confirmed visually.

Figure 2A:
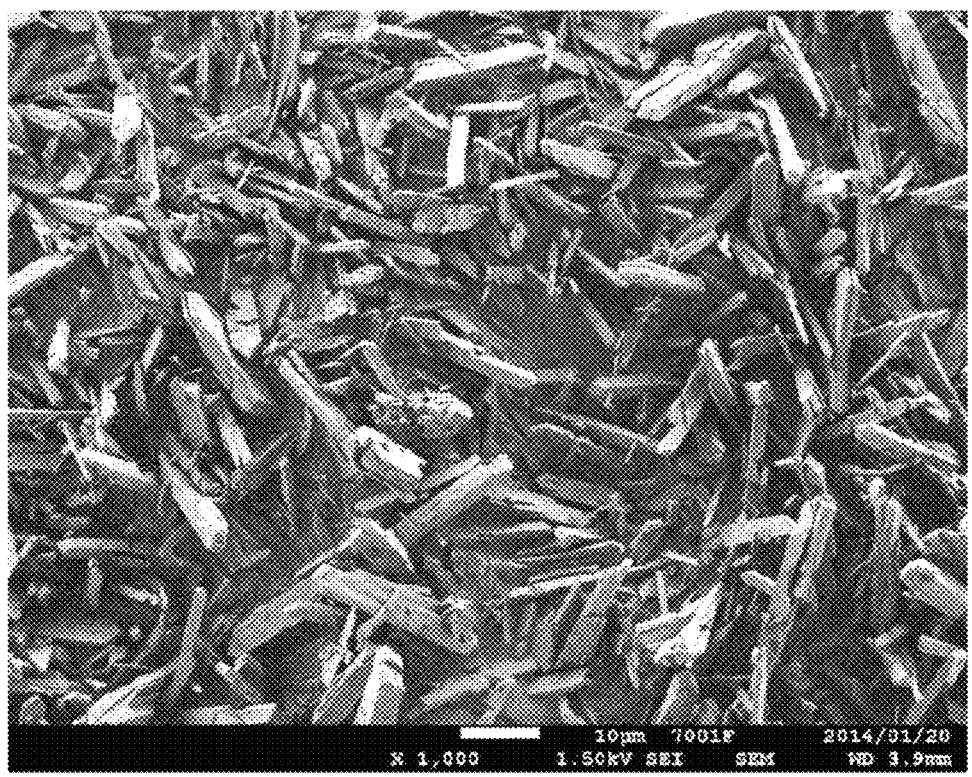
FIG. 2a is an electron microscope image of the crystal shape of the Hofmann type coordination polymer of the present invention observed under a magnification of 1,000.
Figure 2B:
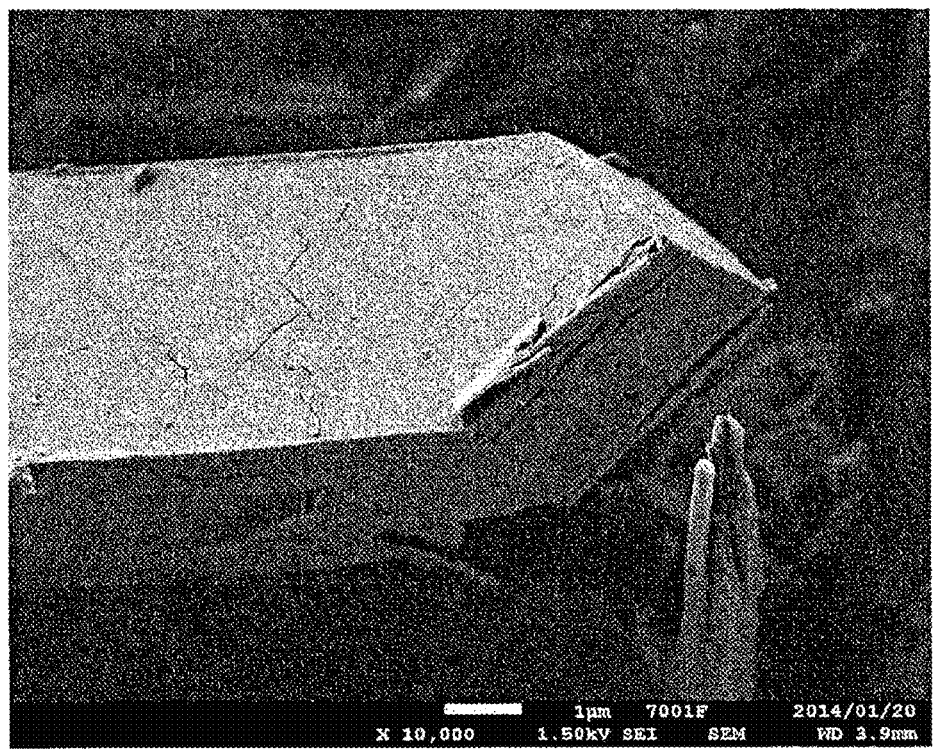
FIG. 2b is an electron microscope image of the crystal shape of the Hofmann type coordination polymer of the present invention observed under a magnification of 10,000.

FIGS. 2a and 2b are photos of the crystal shape of the gas detection material of the present invention taken by scanning electron microscope (SEM). The inventors of the present invention study various synthesis methods for the {Fe(pz)[Ni(CN)$_4$]} (wherein, pz=pyrazine), and the results confirm that the crystal shapes will be different if the concentrations, the solvents, the reaction times or the like during the synthesis process are changed and a so-called crystal polymorphism exists. The crystal shape is preferred to be a slender pillar as shown in FIG. 2a and FIG. 2b as a gas detection material as the change in the color when the gas is adsorbed will be obvious and the adsorbed gas is hard to be desorbed after the color changed. The size in the long axis direction of the pillared crystal shape is preferred to be about 3 μm to 15 μm. The size in the long axis direction of the pillared crystal shape is further preferred to be about 5 μm to 15 μm from the view point of more obviousness of the change in the color when the gas is adsorbed. The size in the long axis direction of the pillared crystal shape is calculated by calculating the average length of 100 crystal grains selected from the picture taken by the scanning electron microscope. On the other hand, the {Fe(pz)[Ni(CN)$_4$]} (wherein, pz=pyrazine) synthesized by the method described in Non-Patent Document 2 is a cubic crystal of about 0.5 μm~2 μm. However, if the crystal is in such a shape, the change in the color when the gas is adsorbed will be not obvious easily, and the adsorbed gas is easy to be desorbed after the color changed, thus, the color will recover. Therefore such {Fe(pz)[Ni(CN)$_4$]} (wherein, pz=pyrazine) is not applicable as a gas detection material.

The crystal structure of the gas detection material of the present invention can be investigated by an X-ray structural analysis. Further, the crystal shape can be confirmed by an optical microscope or a scanning electron microscope. The magnification for confirming can be about 1000 to 10000.

The spin state of the gas detection material of the present embodiment can be confirmed by observing the response of the magnetization relative to the magnetic field using superconducting quantum interference device (SQUID) or vibrating sample magnetometer (VSM).

In the manufacture method of the gas detection materials of the present embodiment, first, carry out a reaction of the ferrous salt, tetracyanonickelate in a proper solvent to obtain an intermediate of the pillared crystal of $\{Fe[Ni(CN)_4]\}$. Then dissolve the intermediate of $\{Fe[Ni(CN)_4]\}$ in a proper solvent and a gas detection material having the composition of $\{Fe(pz)[Ni(CN)_4]\}$ (wherein, pz=pyrazine) can be obtained by adding pyrazine into the dispersion.

As the ferrous salt, iron(II) sulfate heptahydrate, ammonium iron(II) sulfate hexahydrate or the like can be used. As the tetracyanonickelate, potassium tetracyanonickelate (II) hydrate or the like can be used. As the solvent, mixed solvent of water and alcohol can be used.

It is preferable that a part or the whole of the gas detection material of the present embodiment is in low-spin state. As the processing method for turning the gas detection material into the low-spin state, methods can be listed such as cooling the gas detection material sufficiently using liquid nitrogen or the like and then returning to normal temperature, contacting the gas detection material with the chemical substance which can induce the low-spin state of the gas detection material. As the chemical substance which can induce the low-spin state of the gas detection material, acetonitrile can be listed as an example.

As the gas detection material of the present embodiment, it is preferred that acetonitrile is contained. If the gas detection material is contacted with the vapor of acetonitrile, it will adsorb acetonitrile into the crystals and will be induced to turn to be the low-spin state. Thus, if acetonitrile is contained, the gas detection material can be kept in the low-spin state.

Acetonitrile contained in the gas detection material of the present embodiment can be confirmed by using a gas chromatograph mass spectrometer having a double-shot pyrolyzer (manufactured by Frontier Laboratories).

Figure 3:
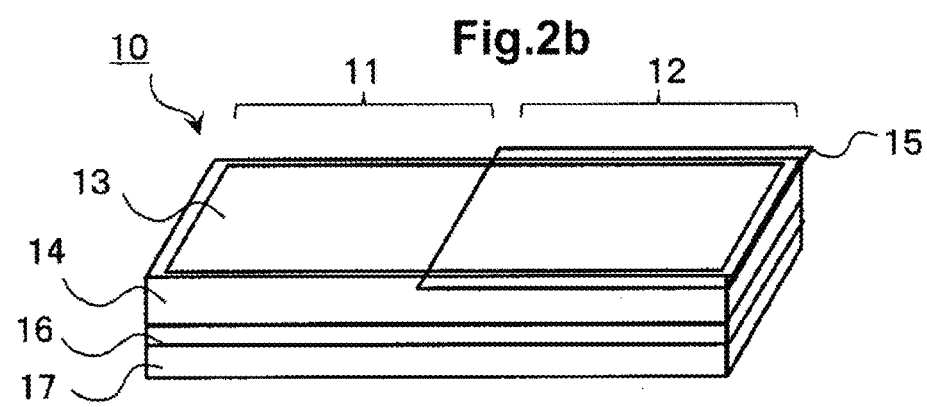
FIG. 3 is a schematic view showing the gas detection tape of the present invention.

FIG. 3 is a schematic view of the gas detection tape of the present embodiment. In FIG. 3, in gas detection tape 10, on at least one surface of supporter 14, gas detection material layer 13 containing detection part 11 and reference part 12 is installed.

The gas detection material of detection part 11 contains Hofmann type porous coordination polymer $\{Fe(pz)[Ni(CN)]\}$ (wherein, pz=pyrazine) in low-spin state which contains ferrous ions, tetracyanonickelate ions and pyrazines as the essential ingredients and has a pillared crystal shape. The gas detection material will adsorb the gas if vapor of diethyl carbonate or the like is existed, and it will change from reddish purple to orange. On the other hand, as the gas detection material layer of reference part 12 will also show reddish purple of low-spin state when gas existing, it can be prevented from contacting with gas atmosphere by covering using protective layer 15. Otherwise, in order to maintain the low-spin state even under the existing of the detected gas without using protective layer 15, a substance which can strongly stabilize the low-spin state can be adsorbed. As the substance, acrylonitrile can be listed. As stated above, if gas detection tape of the present embodiment is used when the gas is existed, the existing of the gas can be easily detected by visually confirming the difference of the colors of the detection part and the reference part.

Supporter 14 is not restricted, for example, cellulose-based pasteboard such as filter paper No. 5C or the like can be used. The material for protective layer 15 is not specially restricted as long as it can prevent the gas detection material layer of reference part 12 from contacting with the gas atmosphere. For example, it can use polyvinylidene chloride film.

On the other face of the supporter, adhesive layer 16 and release paper 17 can be set in turn. When the gas detection tape is used, it can be fixed by releasing the release paper and adhering to the place which is the gas detecting object. Adhesive layer 16 and release paper 17 can use well-known materials respectively.

The gas detection material layer of reference part 12 can be replaced with other coloring materials. If coloring materials having equal color tone with the color in the high-spin state or the low-spin state of the detection material are used, the change of the color tone of the gas detection part 11 can be confirmed visually. Further, the gas detection tape from which reference part 12 is separated only having the detection part 11 can also be used in gas detection if there are methods for confirming the change of the color tone by color samples or the like.

Figure 4:
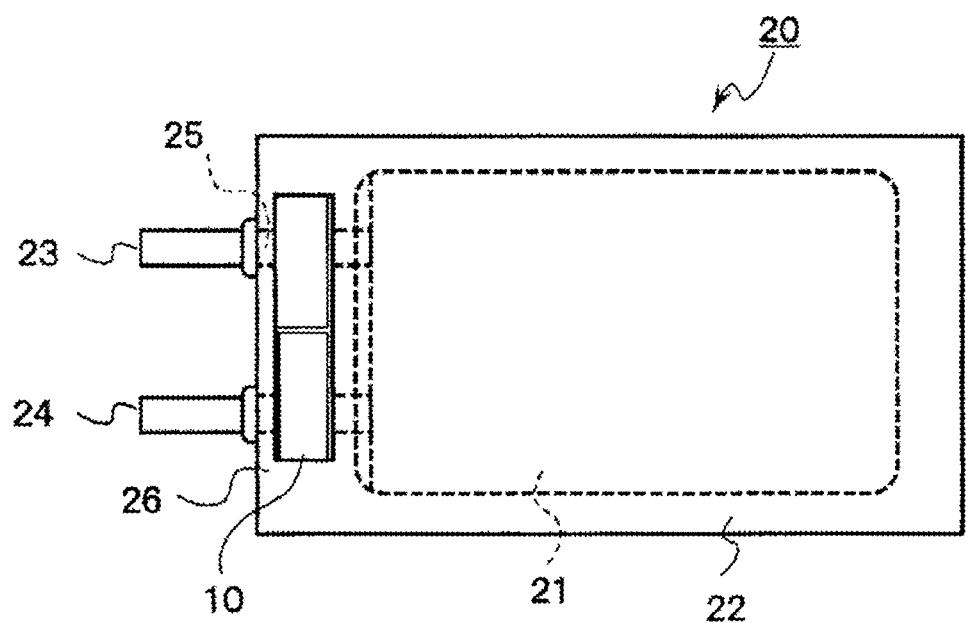
FIG. 4 is a schematic view showing the lithium ion secondary battery of the present invention.

The lithium ion secondary battery of the present invention is characterized in that the gas detection material or the gas detection tape mentioned above is disposed on the face of the outer package of the lithium ion secondary battery. FIG. 4 is the schematic view of the lithium ion secondary battery of the present embodiment.

Lithium ion secondary battery 20 of the present embodiment contains battery part 21, outer package 22 which houses battery part 21. Battery part 21 is composed of a positive plate, a negative plate and a separator between the positive plate and the negative plate. Battery part 21 is wound as a jelly-roll structure or laminated as a stack with the positive plate, the separator and the negative plate set in turn.

Positive electrode tab 23 and negative electrode tab 24 which electrical coupled with the electrode plates of battery part 21 is exposed in the outer space of the sealed plane 26 of outer package 22. The parts where electrode tabs 23, 24 contact with sealed plane 26 is coated by insulating tape 25 respectively.

Gas detection tape 10 adheres to outer package 22. Outer package 22 is composed of a non-sealed plane which houses battery part 21 in the central part and a sealed plane which adhere to the non-sealed plane to form a bag-like shape. Herein, the adhering part with exposure parts for electrodes is called as sealed plane 26. The place for the gas detection tape adhering is not specified especially, but the vapor of the electrolyte solution or the decomposed gas of the electrolyte solution often leak out from the vicinity of sealed plane 26 and the vicinity of sealed plane 26 is easy to be released especially in the vicinity of the electrodes, thus, the gas detection tape is preferred to be fixed to the vicinity of sealed plane 26.

The detection method for the leaked gas from the lithium ion secondary battery of the present embodiment is characterized in that, gas detection tape 10 is disposed on the surface of the outer package of the present embodiment and the produce of the gas is detected from the change of the color of the gas detection material. The lithium ion secondary battery uses the ring or chain carbonate-based electrolyte solution. As chain carbonate such as dimethyl carbonate or diethyl carbonate or the like has a lower boiling point, the sealability of the outer package is not sufficient, and pinhole or the like is produced in the outer package so that the vapor of these electrolyte solution components is leaked out as outgas. If the gas detecting material is contacted with the leaked gas, the leaked gas molecules will be adsorbed into the crystals and at the same time the state of the electron will turn to high-spin state from low-spin state and the color tone of detection part 11 will change. The leaked gas can be simply detected by visually comparing the difference of the color tone with the reference part 12.

Also, a gas detection tape without reference part 12 can also be used, in this case, the producing of gas can be detected by confirming the change of the color tone of detection part 11 using the color samples prepared respectively (for example, JPMA Standard paint colors, 2013, version G, manufactured by Japan Paint Manufacturers Association).

The detection method for the leaked gas from the lithium ion secondary battery of the present embodiment do not need a hermetically sealed container or a power supply of large scale as in the current technology. The leaked gas can also be detected in processes other than the inspection process. The gas detection material which turns to a high-spin state by adsorbing the produced gas will not recover to the low-spin state as long as it is not processed specifically, thus, it is helpful to the users for that it can pick out the lithium ion secondary batteries which have turned bad because of the leaked gas caused by any reasons during transportation or storage before using the batteries.

EXAMPLES

Hereinafter, the present invention is further specifically described based on the examples. However the present invention is restricted by the following examples.

Example 1

(Preparation of the Gas Detection Materials)

Into a container, 0.24 g of ammonium iron (II) sulfate hexahydrate, 0.1 g of L-ascorbic acid and 0.15 g of potassium tetracyanonickelate (II) monohydrate were stirred using 240 mL of mixed solvent of distilled water and ethanol. The obtained pillared intermediate $\{Fe[Ni(CN)_4]\}$ crystals were collected. In the container, the obtained intermediate crystals and 0.10 g of pyrazine were mixed using ethanol as the solvent and 0.11 g of obtained orange crystals were collected. The obtained crystals were used as the gas detection material. The obtained crystals were confirmed as pillared crystals with an average length in the long axis direction of about 15 μm using a scanning electron microscope. The crystal structure of the gas detection material was investigated by an X-ray structural analysis. Further, the crystal shape was confirmed by an optical microscope or a scanning electron microscope. The spin state was confirmed by using superconducting quantum interference device (SQUID) or vibrating sample magnetometer (VSM).

(Turning the Gas Detection Materials to a State of low-spin state)

Into a beaker, 10 mg of gas detection materials and 20 mL of ethanol were added and stirred to obtain a dispersed solution. During stirring, 2 mL of the dispersed solution was fetched using a syringe and then was flowed from the top side of a filter paper No. 5C (with a diameter of 20 mm) which was set in a suction filter. In this way, a gas detection material layer was formed on the filter paper No. 5C. Thereafter, the gas detection material sheet was exposed in the acetonitrile vapor for 10 seconds. Thereby, the gas detection material will turn to a low-spin state and change into reddish purple.

(Preparation of the Gas Detection Tape)

On the back side of the gas detection tape, a double-faced adhesive tape with release layer (NICETACK, manufactured by Nichiban Co., Ltd.) was paste and then cut into small rectangular slices with a width of 5 mm, a length of 20 mm and a thickness of 0.5 mm. After that, a reference part was set for one half end of the detection material layer by covering with a film of polyvinylidene chloride (Saran Wrap, manufactured by Asahi Kasei Home Products Corporation) using a glue tape (TG-510D, manufactured by PLUS) as the adhesive and the gas detection tape was completed.

(Detection of Diethyl Carbonate Gas)

A small fan and the gas detection tape were put into a Tedlar bag of 5 L. Air containing diethyl carbonate was fed into it to fill it and the change of the color tone of the gas detection tape was confirmed. The result was shown in Table 1. It could be confirmed that all the color tones of the detection parts of the gas detection tape changed into orange in the air containing 2000 ppm, 200 ppm, 40 ppm, 20 ppm, 4 ppm of diethyl carbonate. The change could be easily confirmed from the difference with the color tone of the reference part. On the other hand, in the case where air without diethyl carbonate (0 ppm) was fed into the bag, the color of the detection part did not change and no difference of the color tone could be observed comparing to the reference part. Thereby, it could be confirmed that diethyl carbonate can be detected from the change of the color tone.

TABLE 1

| The concentration of diethyl carbonate (ppm) | Time required for detection (min.) | Change of the color tone of the detection part |
| --- | --- | --- |
| 2000 | <1 | reddish purple→orange |
| 200 | <1 | reddish purple→orange |
| 40 | <1 | reddish purple→orange |
| 20 | 10 | reddish purple→orange |
| 4 | 45 | reddish purple→orange |
| 0 | — | none |

(Detection of Other Gases)

A screw vial of 50 mL was filled with organic combustible gas or vapor of organic solvent and the gas detection tape was put in to observe the change. A color change from reddish purple to orange was confirmed that when the gas detection tape was exposed in ethylene, propylene, toluene, xylene, acetone, ethyl acetate, tetrahydrofuran, methanol, ethanol, n-propanol, isopropanol, ammonia, dim ethylamine, trim ethylamine, triethylamine, acetic acid, formaldehyde, acetaldehyde, diethyl ether, dimethyl carbonate and ethyl methyl carbonate and diethyl carbonate.

(Detection of the Leaked Gas of the Lithium Ion Secondary Battery)

Ten lithium ion secondary batteries were prepared with a gas detection tape attached near the sealed plane of the outer package respectively. Among these batteries, a pinhole was punched artificially using needle to simulate the condition when a pinhole was existed on the outer package for one battery. The batteries were put into the unit packs respectively and sealed, and then placed for one hour. The gas detection tape of the lithium ion secondary battery was confirmed visually. The detection part of the gas detection tape of the lithium ion secondary battery with a pinhole turned to be orange which was different from the reference part. 10 μL of air in the unit pack with this lithium ion secondary battery was fetched using a gas-tight syringe and the component was analyzed using a gas chromatograph (GC-2014, manufactured by Shimadzu Corporation). As the result, about 400 ppm of diethyl carbonate was detected. On the other hand, the air in the unit pack with the lithium ion secondary batteries of which the gas detection tape did not change was fetched respectively. As the result, no gas content from electrolyte solution could be detected.

Example 2

Except that 60 ml of mixed solvent of distilled water and ethanol was used, a gas detection material was prepared in the same way as Example 1. The obtained gas detection material was confirmed as a pillared crystal with an average length in long axis direction of about 5 μm using a scanning electron microscope. A gas detection tape was completed using the obtained gas detection material in the same way as Example 1.
(Detection of Diethyl Carbonate Gas)

The prepared gas detection tape in Example 2 was used to try to detect the diethyl carbonate gas in the same way as in Example 1. The result confirmed that diethyl carbonate can be detected from the change of the color tone.

Comparative Example 1

Except that 12 ml of mixed solvent of distilled water and ethanol was used, a gas detection material was prepared in the same way as Example 1. The obtained gas detection material was confirmed as a flaky crystal with an average length in plane direction of about 2 μm using a scanning electron microscope. The obtained gas detection material was used to perform the process for turning the gas detection material into a low-spin state. As a result, there was no much change in the color and no more investigation could be performed.

Comparative Example 2

A detection material for comparing was prepared as follows referring to the method described in the Non-Patent Documents.

Into a container, 0.24 g of ammonium iron(II) sulfate hexahydrate, 0.1 g of L-ascorbic acid, 0.15 g of potassium tetracyanonickelate (II) monohydrate and 0.10 g of pyrazine were stirred using 240 mL of mixed solvent of distilled water and ethanol. The obtained crystals (0.11 g) were collected. The obtained crystals were used as the detection material. The obtained crystals were confirmed as a cubic crystal with an average length in one side of about 2 μm using a scanning electron microscope. The obtained gas detection material was used to perform the process for turning the gas detection material into a low-spin state. As a result, the gas detection material did change into weak reddish purple turn as Example 1, however, it reverted to orange very soon from that state and no more investigation could be performed.

It could be known from the results above that, the detection material in the Examples could detect the leaked gas easily without using a large-scale detection instrument. The gas detection tape using the gas detection material could detect the leaked gas easily by attaching to the lithium ion secondary battery.

DESCRIPTION OF REFERENCE NUMERALS

1 . . . $\{Fe(pz)[Ni(CN)_4]\}$ (wherein, pz=pyrazine)
2 . . . Ferrous ion
3 . . . Tetracyanonickelate ion
4 . . . Pyrazine
10 . . . Gas detection tape
11 . . . Detection part
12 . . . Reference part
13 . . . Gas detecting material
14 . . . Supporter
15 . . . Protective layer
16 . . . Adhesive layer
17 . . . Release paper
20 . . . Lithium ion secondary battery
21 . . . Battery part
22 . . . Outer package
23 . . . Positive electrode tab
24 . . . Negative electrode tab
25 . . . Insulating tape
26 . . . Sealed plane of the outer package

What is claimed is:

1. A gas detection material comprising a Hofmann type porous coordination polymer of $\{Fe(pz)[Ni(CN)_4]\}$ which contains ferrous ion, tetracyanonickelate ion and pyrazine as the essential ingredients and has a pillared crystal shape, wherein, pz=pyrazine.

2. The gas detection material according to claim 1, wherein a part or the whole of the gas detection material is in low-spin state.

3. The gas detection material according to claim 2, wherein the gas detection material contains acetonitrile.

4. The gas detection material according to claim 1, wherein the gas detection material contains acetonitrile.

5. A lithium ion secondary battery, wherein,
the outer package of the lithium ion secondary battery comprises the gas detection material of claim 1.

6. The gas detection material according to claim 1, wherein the pillared crystal shape has a size in a long axis direction of about 3 to 15 μm.

7. The gas detection material according to claim 6, wherein the size is about 5 to 15 μm.

8. A gas detection tape made by laminating a gas detection material on at least one surface of the supporter, wherein,
the gas detection material contains a Hofmann type porous coordination polymer of $\{Fe(pz)[Ni(CN)_4]\}$ which contains ferrous ion, tetracyanonickelate ion and pyrazine as the essential ingredients and has a pillared crystal shape,
wherein, pz=pyrazine.

9. A lithium ion secondary battery, wherein,
the outer package of the lithium ion secondary battery comprises the gas detection tape of claim 8.

* * * * *